United States Patent
Ilincic et al.

(10) Patent No.: US 11,615,392 B2
(45) Date of Patent: Mar. 28, 2023

(54) SYSTEMS AND METHODS FOR USING INFORMATION FROM WEARABLE DEVICES

(71) Applicant: Capital One Services, LLC, McLean, VA (US)

(72) Inventors: Rajko Ilincic, Annandale, VA (US); Jeffrey Rule, Chevy Chase, MD (US); Daniel Herrington, New York, NY (US)

(73) Assignee: CAPITAL ONE SERVICES, LLC, Mclean, VA (US)

( * ) Notice: Subject to any disclaimer, the term of this patent is extended or adjusted under 35 U.S.C. 154(b) by 236 days.

(21) Appl. No.: 16/864,966

(22) Filed: May 1, 2020

(65) Prior Publication Data
US 2021/0342811 A1 Nov. 4, 2021

(51) Int. Cl.
*G06Q 20/32* (2012.01)
*G06Q 20/40* (2012.01)
*G06Q 20/20* (2012.01)
*A61B 5/00* (2006.01)

(52) U.S. Cl.
CPC .......... *G06Q 20/321* (2020.05); *A61B 5/681* (2013.01); *G06Q 20/204* (2013.01); *G06Q 20/206* (2013.01); *G06Q 20/4097* (2013.01)

(58) Field of Classification Search
CPC ............... G06Q 20/00–425; A61B 5/00–7495
See application file for complete search history.

(56) References Cited

U.S. PATENT DOCUMENTS

| 5,764,789 | A | 6/1998 | Pare, Jr. et al. |
| 6,990,588 | B1 | 1/2006 | Yasukura |
| 7,128,274 | B2 | 10/2006 | Kelley et al. |

(Continued)

FOREIGN PATENT DOCUMENTS

| CN | 103417202 | 12/2013 |
| EP | 1 085 424 | 4/2008 |
| GB | 2516861 | 2/2015 |

OTHER PUBLICATIONS

Aksic et al., "Usability of Commercial mHealth Tookits from a Developer Perspective," Norwegian University of Science and Technology, 2016.*

(Continued)

*Primary Examiner* — John W Hayes
*Assistant Examiner* — Chenyuh Kuo
(74) *Attorney, Agent, or Firm* — Hunton Andrews Kurth LLP

(57) ABSTRACT

Systems and methods for the of use information from application programming interfaces on wearable devices in third party applications are provided. A system comprising a user device, data storage, an application programming interface and an application is provided. In this system, there is a user device that includes a health monitor. The health monitor includes sensors and associated software that enable it to obtain health information about the wearer of the user device. In this system, there is data storage on the user device that stores the health information as user health data. In this system, there is an application programming interface on the user device that enables the health monitor to share the user health data with other applications executing on the user device.

20 Claims, 12 Drawing Sheets

(56) References Cited

U.S. PATENT DOCUMENTS

| | | | |
|---|---|---|---|
| 7,152,045 | B2 | 12/2006 | Hoffman |
| 7,689,832 | B2 | 3/2010 | Talmor et al. |
| 7,796,013 | B2 | 9/2010 | Murakami et al. |
| 8,371,501 | B1 | 2/2013 | Hopkins |
| 8,475,367 | B1 | 7/2013 | Yuen et al. |
| 8,994,498 | B2 | 3/2015 | Agrafioti et al. |
| 9,208,492 | B2* | 12/2015 | Hoyos ................... H04W 12/06 |
| 9,473,509 | B2 | 10/2016 | Arsanjani et al. |
| 9,710,804 | B2 | 7/2017 | Zhou et al. |
| 9,916,474 | B2* | 3/2018 | Tribble .................. G16H 10/20 |
| 9,953,323 | B2 | 4/2018 | Candelore et al. |
| 9,996,678 | B2* | 6/2018 | Johnson ................ H04W 76/10 |
| 10,133,979 | B1 | 11/2018 | Eidam et al. |
| 11,056,238 | B1* | 7/2021 | Nakajima ............... G16H 40/67 |
| 11,151,542 | B2* | 10/2021 | Senguttuvan ........... G06F 1/163 |
| 2010/0192230 | A1 | 7/2010 | Steeves et al. |
| 2011/0084132 | A1 | 4/2011 | Tofighbakhsh |
| 2011/0246780 | A1 | 10/2011 | Yeap et al. |
| 2012/0024947 | A1 | 2/2012 | Naelon |
| 2013/0304651 | A1 | 11/2013 | Smith |
| 2015/0332266 | A1 | 11/2015 | Friedlander et al. |
| 2018/0324177 | A1* | 11/2018 | Wang ................. G02B 27/0172 |
| 2020/0380523 | A1* | 12/2020 | Agrawal ............ G06Q 20/3226 |
| 2022/0027917 | A1* | 1/2022 | Chen ..................... H04L 9/3297 |

OTHER PUBLICATIONS

Aksic et al., Usability of Commercial mHealth Tookits from a developer perspective, NTNU, 2016 (Year: 2016).*

* cited by examiner

SYSTEMS AND METHODS FOR USING INFORMATION FROM WEARABLE DEVICES

FIELD OF THE INVENTION

The present disclosure generally relates to wearable devices and, in particular, to using information from application programming interfaces on wearable devices in third party applications for a different purpose.

BACKGROUND

Consumers are increasingly adopting electronic payment methods, such as credit cards and debit cards, for purchases, wire transfers, bill pay or any other financial transactions. Consumers will commonly carry at least one credit or debit card, and often consumers carry more than one. Consumers may prefer to use credit or debit cards for reasons of convenience, to earn rewards based on spending, to simplify budgeting through the receipt of a monthly statement, or to avoid carrying large amounts of cash. In many areas, credit or debit card transactions outnumber cash transactions.

At the same time, the widespread use of communication devices, such as smart phones, smart watches, laptop computers, and tablets, make data increasingly accessible, including financial information such as account balances and purchase activity, wire transfers, bill pay or any other financial transactions. The availability of these devices creates expectations for consumers that their data will be easily accessible at home, outside the home, and on mobile devices.

In view of these trends, data security is increasingly important in many areas, and protecting financial or other sensitive data is a particular concern. Despite large investments in developing, implementing, and maintaining security measures, data theft and fraud causes millions, if not billions, of losses annually. Any organization handling sensitive data, financial or otherwise, incurs data security costs and risks liability for theft or other losses due to breaches of data security. In addition to monetary costs, data security breaches erode user confidence in a business, and a large or otherwise notable breach often attracts significant public attention.

Accordingly, there are significant, and competing, needs to safeguard sensitive data while ensuring ready access by authorized users.

SUMMARY

The disclosed subject matter is directed to systems and methods for using information from application programming interfaces on wearable devices in third party applications for a different purpose that satisfy these needs.

One embodiment of the present disclosure is a system comprising a user device, data storage, an application programming interface and an application. In this system, there is a user device that includes a health monitor. The health monitor includes sensors and associated software that enable it to obtain health information about the wearer of the user device. In this system, there is data storage on the user device that stores the health information as user health data. In this system, there is an application programming interface on the user device that enables the health monitor to share the user health data with other applications executing on the user device. In this system, there is an application that executes a query on the user device to obtain a user device identifier and the user health data. Using the user health data, the application determines the presence or absence of requisite health data. The application transmits the user device identifier and a signal indicating the presence or absence of the requisite health data to a server. Upon receipt of the user device identifier and signal indicating the presence or absence of the requisite health data, the server identifies a user account based on the user device identifier and either enables or disables transaction authentication. The server enables transaction authentication if the signal indicates the presence of health data. Alternatively, the server disables transaction authentication if the signal indicates the absence of health data.

In an example method according to the disclosure, user accounts are stored in a database of a backend system. Each user account includes user account information that includes information to identify the account holder, an account holder wearable device identifier, and a flag. The flag indicates whether transactions are to be approved or denied based on the respective presence or absence of a vital sign of the account holder. The vital sign is detected by a wearable device identified by the account holder wearable device identifier. An application is provided for execution on the wearable device. The wearable device includes a health monitor with an application programming interface. Via the application programming interface, the application queries the wearable device to obtain a wearable device identifier and health data. The health data indicates the presence or absence of a vital sign of the wearer of the wearable device. The application wirelessly transmits the wearer's wearable device identifier and health data to the backend system. The backend system receives the wearer's wearable device identifier and health data that indicates the presence or absence of the wearer's vital sign. Using a processor at the backend system, it is determined whether the wearer's wearable device identifier matches the account holder wearable device identifier. If the wearer's wearable device identifier matches the account holder wearable device identifier, then the processor at the backend system is used to access the account holder user account and set the flag that is stored in the account holder user account. The flag indicates whether transactions are to be approved or denied based on the received health data that indicates the presence or absence of the wearer's vital sign.

Further, an example system according to various embodiments comprises a wireless wearable device communication interface, a transaction processor, a database, and a transaction request communication interface. In this system, the wireless wearable device communication interface communicates, via a network, with a wearable device to receive a wearable device identifier and a signal. The wearable devices has the wearable device identifier and the signal. The signal indicates whether the wearable device is detecting a vital sign of the wearer of the wearable device. In this system, the transaction processor approves or denies transaction requests. In this system, the database stores a plurality of user accounts. Each user account includes information that identifies the account holder, an account holder wearable device identifier, and a user preference indicator. The user preference indicator indicates whether the transaction processor is to approve or deny a requested based on the respective presence or absence of a vital sign of the account holder. This presence or absence is detected by the wearable device identified by the account holder wearable device identifier. In this example system, the transaction request communication interface receives a transaction request from a point of sale terminal. When the transaction request communication interface receives the transaction request from the point of sale terminal, the transaction processor identifies a user account. The user account is identified based on information received with the user account. The transaction processor queries the account holder user account to determine whether user preference indicator stored in the account holder user account indicates whether to approve or deny the transaction. The transaction processor transmits, based on the query result, a signal, via the transaction request communication interface, approving or denying the transaction to the point of sale terminal. The wearable device includes an application that queries, via an application programming interface, the wearable device to obtain a wearable device identifier and signal. The signal indicates whether the wearable device is detecting a vital sign of the wearer of the wearable device. The application wirelessly transmits the wearable device identifier and signal to the wireless wearable device communication interface.

These and other features, aspects and advantages of the disclosed subject matter are explained in greater detail with reference to specific example embodiments that are illustrated in the following description, appended claims, and accompanying drawings.

DETAILED DESCRIPTION OF EXAMPLE EMBODIMENTS

The following description of embodiments provides non-limiting representative examples referencing numerals to particularly describe features and teachings of different aspects of the invention. The embodiments described should be recognized as capable of implementation separately, or in combination, with other embodiments from the description of the embodiments. A person of ordinary skill in the art reviewing the description of embodiments should be able to learn and understand the different described aspects of the invention. The description of embodiments should facilitate understanding of the invention to such an extent that other implementations, not specifically covered but within the knowledge of a person of skill in the art having read the description of embodiments, would be understood to be consistent with an application of the invention.

Figure 1:
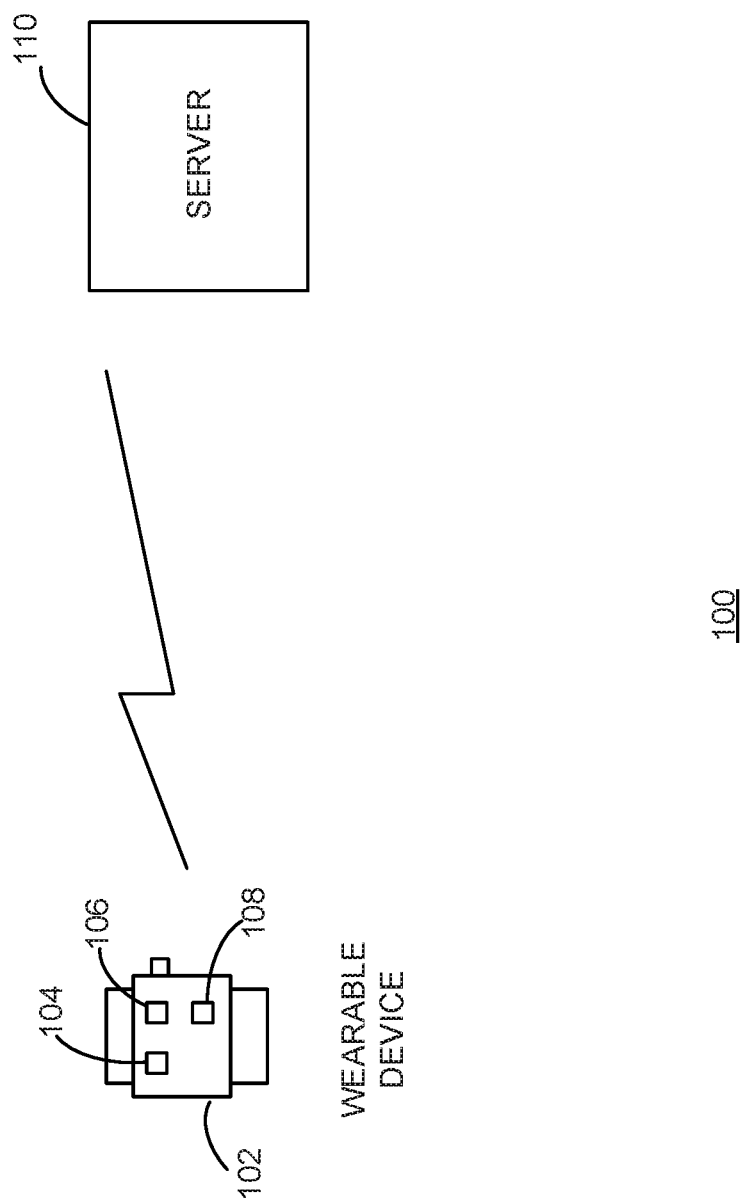
FIG. 1 is a diagram of a system for using a wearable device, according to an example embodiment.

FIG. 1 is a diagram of a system 100 for using a wearable device 102, according to an example embodiment. Wearable device 102 may be any electronic device that may be worn on a body, implanted, incorporated into an item of clothing or an accessory or into a living or working environment, such as a fitness tracker, a smartwatch, glasses, shirt, pants, shoes, gloves, necklaces, earrings, ear pieces, headsets, internet of things (IoT) devices, and other similar devices. For example, wearable device 102 may be an Apple Watch®, a FitBit®, a heart rate monitor that a user wears while riding a Peloton® bike, and any other similar device.

Wearable device 102 may include a sensor 104, an application 106 and a communication interface 108. Sensor 104 may be capable of determining some kind of health data, for example, vital signs like heart rate, blood pressure, glucose or other health data.

As will be described in more detail below, wearable device 102 may include software and interfaces that enable application 106 to obtain information, such as health-related and/or vital sign information, from sensor 104. Application 106 may be one or more applications capable of receiving health data from sensor 104 and sending a signal indicating the absence or presence of health data from sensor 104 to a server 110 using communication interface 108. Application 106 and server 110 may be configured to use health data for a different purpose. For example, health data may be used to authenticate a transaction, such as payment, credit, authorization, membership, or access.

Communication interface 108 may facilitate data communication between wearable device 102 and server 110 and may occur over one or more networks (not shown), such as one or more of a fiber optics network, a passive optical network, a cable network, an Internet network, a satellite network, a wireless local area network (LAN), a Global System for Mobile Communication, a Personal Communication Service, a Personal Area Network, Wireless Application Protocol, Multimedia Messaging Service, Enhanced Messaging Service, Short Message Service, Time Division Multiplexing based systems, Code Division Multiple Access based systems, Digital-Advanced Mobile Phone Service (D-AMPS), Wi-Fi, Fixed Wireless Data, IEEE 802.11b, 802.15.1, 802.11n and 802.11g, Bluetooth, near-field communication (NFC), Radio Frequency Identification (RFID), and/or the like. In addition, the network may include, without limitation, telephone lines, fiber optics, IEEE Ethernet 902.3, a wide area network, a wireless personal area network, a LAN, or a global network such as the Internet. In addition, the network may support an Internet network, a wireless communication network, a cellular network, or the like, or any combination thereof.

Communication interface 108 may communicate using a network that may further include one network, or any number of the exemplary types of networks mentioned above, operating as a stand-alone network or in cooperation with each other. The network may utilize one or more protocols of one or more network elements to which they are communicatively coupled. The network may translate to or from other protocols to one or more protocols of network devices. The network may comprise a plurality of interconnected networks, such as, for example, the Internet, a service provider's network, a cable television network, corporate networks, such as credit card association networks, and home networks.

Server 110 may be one or more servers in a client—server system (not shown), which may be a distributed application structure on a network that manages tasks or workloads between the providers of a resource or service, called servers, and service requesters, called clients. For example, in a banking or credit card system for making a purchase, wire transfer, bill pay or any other financial transaction, application 106 may act as a client and server 110 may act as a backend server. Application 106 may request a resource or service from server 110 and then make a payment. For such requests and payments, application 106 and server 110 may use one or more applications, application programming interfaces, web services platform-based services, and/or cloud computing services.

Further, when a user is wearing wearable device 102, the payment may be approved and when the user is not wearing wearable device 102, the payment may be denied. Application 106 may determine whether the user is wearing, for example, a heart rate monitor by checking whether sensor 104 is reading heart rate data and then use communication interface 108 to send a signal to server 110 indicating whether the user is wearing the heart rate monitor. The user may set up or register a desire to use the heart rate monitor for the purpose of authenticating payments ahead of time so that server 110 knows to check for it. Application 106 may use an application programming interface on wearable device 102 to obtain information about vital signs, such as heart rate data, determine whether it is present or not, and then use that as a trigger to approve or deny the payment.

Figure 2:
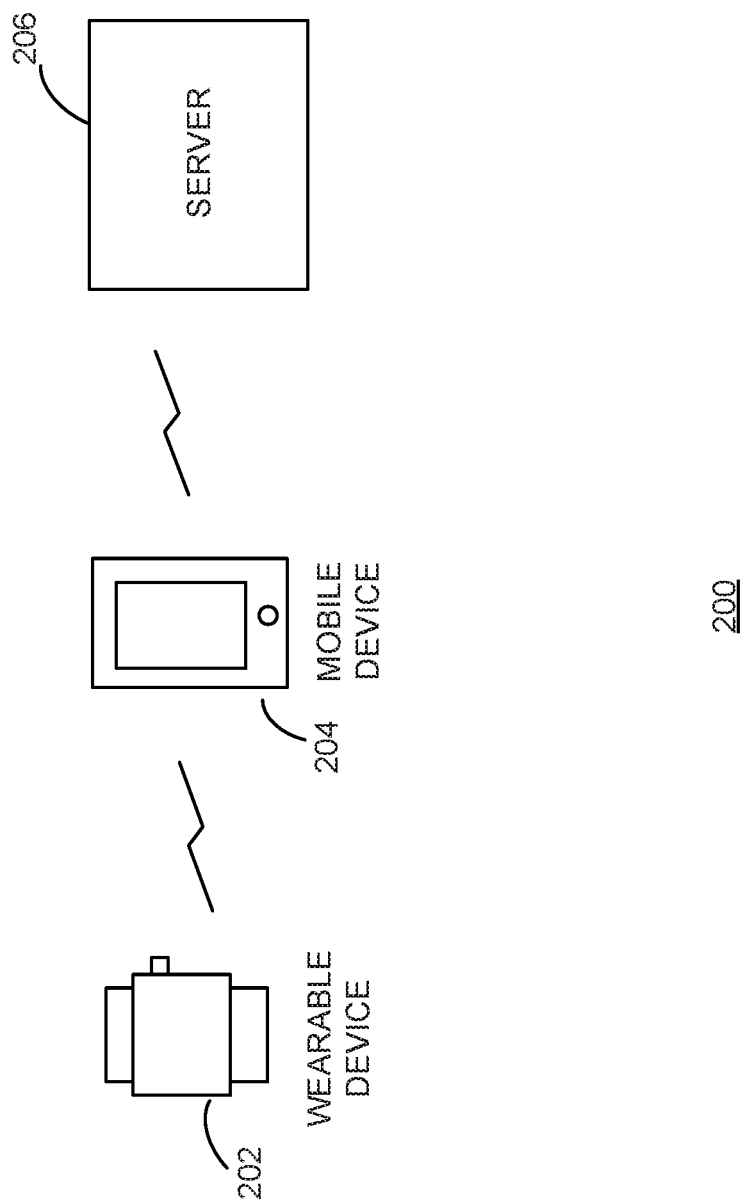
FIG. 2 is a diagram of a system for using a wearable device, according to an example embodiment.

FIG. 2 is a diagram of system 200 for using a wearable device 202, according to an example embodiment. System 200 may include components similar to those shown and described in system 100 of FIG. 1. System 200 may further include a mobile device 204. Mobile device 204 may be in data communication with wearable device 202 and server 206. In various examples, mobile device 204 may be an iPhone®, iPod®, or iPad® from Apple or any other mobile device running Apple's iOS® operating system, any device running Microsoft's Windows® Mobile operating system, any device running Google's Android® operating system, and/or any other smartphone, tablet, or any kind of mobile device running any kind of operating system.

Mobile device 204 may be configured to conduct a transaction with server 206, by installing an application on mobile device 204, visiting a website, or using some other configuration. Accordingly, mobile device 204 may send a request for an indication of the absence or presence of health data from wearable device 202, receive the indication, and forward the indication to the server 206 to authenticate the transaction. For example, when wearable device 202 is being worn by a wearer, transactions will be approved and when wearable device 202 is not being worn is off, transactions will be denied. In this way, the mere presence or absence of the signal may be used to inform server 206 in the decision of whether to authenticate the transaction.

Figure 3:
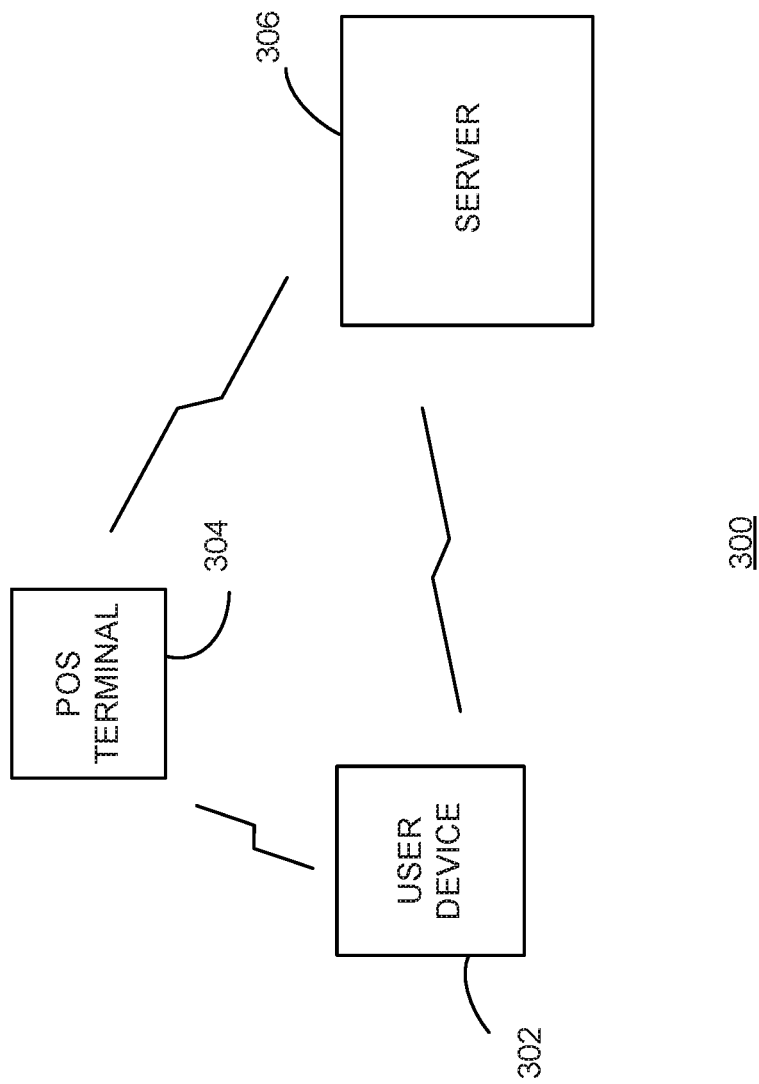
FIG. 3 is a diagram of a system for using a user device, according to an example embodiment.

FIG. 3 is a diagram of a system 300 for using a user device 302, according to an example embodiment. System 300 may include one or more servers 306 in data communication with a user device 302 and a point of sale (POS) terminal 304. User device 302 may be similar to wearable device 102 as shown and described in FIG. 1 and/or similar to mobile device 204 as shown and described FIG. 2, or a combination of the two. In an example where user device 302 is similar to wearable device 102 as shown and described in FIG. 1, a wearable device may communicate wirelessly with server 306. In an example where user device 302 is similar to mobile device 202 as shown and described in FIG. 2, a wearable device, such as a fitness tracker (not shown) may communicate wirelessly with server 306 via user device 302.

POS terminal 304 may be any device used to process payments in any time and at any place where a retail transaction may be completed. At POS terminal 304, a merchant may calculate the amount owed by the customer, indicate that amount, prepare an invoice, indicate payment options to the customer, and complete the transaction. For example, a card holder may put a credit card in a card scanner on POS terminal 304, and then POS terminal 304 may send a processing request to one or more servers 306, which may be associated with the company of the card, (e.g., VISA®, MasterCard®, etc.) and the company may send the request to the issuing bank, which may also be a part of servers 306. The server 306 of the issuing bank may check if there are enough funds in the card holder's account, if the card is registered, and if the card holder has registered user device 302 to be used to authenticate payment using heart rate data from a fitness tracker worn by the card holder. Server 306 may send a signal either to user device 302 or POS terminal 304 requesting authentication. In response, user device 302 may send a signal indicating the presence of heart rate data. The transaction may then be approved or denied based on the presence or absence of heart rate data at POS terminal 304.

Figure 4:
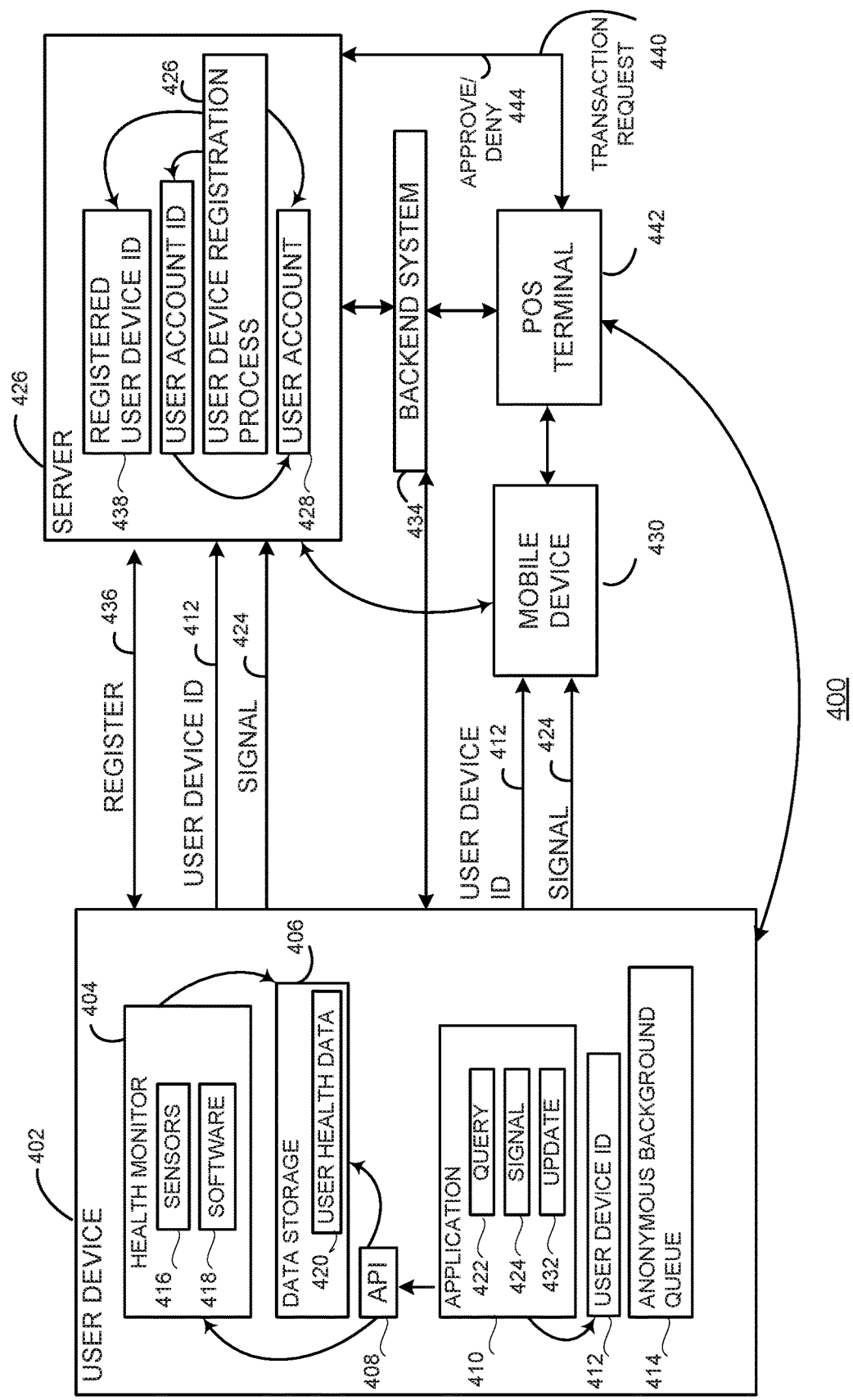
FIG. 4 is a diagram of a system for using a user device, according to an example embodiment.

FIG. 4 is a diagram of a system 400 for using a user device 402, according to an example embodiment. In system 400, user device 402 may include a health monitor 404, data storage 406, an application programming interface (API) 408, an application 410, a user device identifier 412, and an anonymous background queue 414. For example, user device 402 may be a smart watch, a fitness tracker or any like type of device.

Health monitor 404 on user device 402 may include sensors 416 and associated software 418 that may enable health monitor 404 to obtain health information about a wearer of the user device 402. Health monitor 404 may include, for example, a heart rate monitor for a wrist or chest strap or a fitness tracker. Sensors 416 may be any type of sensor, for example, a chest strap may include an electrode pad and transmitter and a wristband fitness tracker may include an optical heart rate monitor. The optical heart rate monitor may have a pulse sensor that shines light from a small light-emitting diode (LED) on the underside of the fitness tracker onto the skin of the wrist to determine a pulse reading from blood following through the wrist. Software 418 may perform one or more health monitoring functions associated with health monitor 404, for example, monitoring vital signs, tracking fitness activity, sleep quality and other health monitoring functions.

Data storage 406 on user device 402 may store the health information as user health data 420. Data storage 406 may be a read-only memory, write-once read-multiple memory or read/write memory, e.g., RAM, ROM, and EEPROM. For example, a fitness tracker may have data storage 406 that includes heart rate data associated with a heart rate monitor along with other health data.

API 408 on user device 402 may enable health monitor 404 to share user health data 420 with other applications, such as application 410, executing on user device 402. For example, a payment application on a smart watch may be set up to authenticate a transaction when the smart watch detects a heart rate. The payment application may use API 408 to access user health data 420 and interface with health monitor 404 to determine whether a heart rate is detected and send this information to server 426, mobile device 430 or POS terminal 442.

Application 410 on user device 402 may include a query 422, a signal 424 and an update 432. Application 410 may use one or more queries 422 to obtain user device identifier 412 and user health data 420. Application 410 may use health data for a purpose other than monitoring health data. For example, in response to a request to verify a payment, application 410 may send user device identifier 412 and signal 424 to server 426, where signal 424 indicates the presence or absence of requisite health data. As referred to herein, requisite health data may refer to those portions of user health data 420 that may be used for various purposes achieved by application 410, which may or may not be related to general health monitoring functionality. For example, application 410 may be a payment application on a smart watch. Upon receipt of user device identifier 412 and signal 424 indicating the presence or absence of the requisite health data, server 426 may identify a user account 428 based on user device identifier 412 and either enable transaction authentication if the signal 424 indicates the presence of health data or disable transaction authentication if the signal indicates the absence of health data. User device identifier 412 uniquely identifies user device 402. For example, user device identifier 412 may be a sequence of characters or code that uniquely identifies a smart watch. For example, a user may set up his or her smart watch so that a credit card purchase, wire transfer, bill pay or any other financial transaction will only be approved when it is made while the user is wearing his or her smart watch. The user may authenticate a purchase, wire transfer, bill pay or any other financial transaction by uniquely identifying the smart watch and providing evidence of health data, such as a pulse taken by the smart watch.

System 400 may further include mobile device 430, which may be wirelessly connected to user device 402. Mobile device 430 may be similar to mobile device 204 as shown and described in FIG. 2. User device 402 may transmit user device identifier 412 and signal 424 indicating the presence or absence of the requisite health data to mobile device 430. Upon receipt of user device identifier 412 and signal 424 indicating the presence or absence of the requisite health data, mobile device 430 may transmit user device identifier 412 and signal 424 indicating the presence or absence of the requisite health data to server 426. For example, a user may use a smart watch in combination with a mobile phone to approve a purchase, wire transfer, bill pay or any other financial transaction by uniquely identifying the smart watch and providing evidence of a heart rate and/or pulse taken by the smart watch.

Query 422 may be a long-running query that executes on an anonymous background queue 414 on user device 402. Application 410 may receive an update 432 when the requisite health data changes, and upon receipt of update 432, application 410 may transmit user device identifier 412 and a change of status signal 424 to server 426. For example, an application on a smart watch may periodically monitor the user's heart rate and/or pulse in the background, while other functions of the smart watch may be operating. The smart watch application may include alerts or updates when it detects certain changes in the user's heart rate and/or pulse, such as when the user puts on or takes off the watch.

In an example embodiment, user device 402 may be, for example, a smart watch, such as an Apple Watch®, smart clothing, or a medical device having sensors 416 that may detect and store vital signs as health information. As referred to herein, vital signs may be any health information that helps people to monitor their health status for athletic activity, fitness, sports, wellness, or medical assessment, diagnostics, or treatment, such as bodily motion, heart rate, step count, activity classification, blood pressure, respiration rate, blood oxygen saturation, blood glucose, skin perspiration, body temperature, and other biometrics or sensor measurements.

In an example embodiment, signal 424 indicating the presence or absence of the requisite health data may be a Boolean flag. Signal 424 may be stored in various other kinds of data structures, such as a number or database record and may be transmitted in various types of messages over any type of communication networks that may be used to connect user device 402, mobile device 430, server 426, backend system 434 and/or POS terminal 442. For example, when a user is using a payment application on a mobile phone to make a purchase, wire transfer, bill pay or any other financial transaction, the financial transaction may be authenticated by uniquely identifying a health monitor and/or fitness tracker being worn by the user and sending a quick indication that the health monitor and/or fitness tracker is detecting a heart rate to allow the financial transaction to be approved in a matter of seconds.

In an example embodiment, user device 402 and server 426 may communicate through request and response messages during a device registration process 426 to register 436 user device 402 with server 426. During user device registration process 426, server 426 may receive user device identifier 438 from user device 402 and store registered user device identifier 438 at server 426, thereby associating user device 402 with user account 428 of the account holder. For example, a user may register a smart watch to be used to verify purchases, wire transfers, bill pay or any other financial transactions made with a particular credit card in order to prevent fraudulent transactions. On their mobile device, the user installs an application that is associated with the issuing bank to register the smart watch with its unique device ID and set a preference to authenticate payments made with the card using the smart watch. After registration, the bank may authenticate payments made with the card according to the user's preference. After registration, the user may change their preference by opening the application to toggle the feature to use vital signs for transaction approval on or off.

In an example embodiment, upon receipt of user device identifier 412 and signal 424 indicating the presence or absence of the requisite health data, server 426 may compare the received user device identifier 412 with the registered user device identifier 438, and, if the received user identifier 412 and registered user identifier 438 are the same, either enable transaction authentication if the signal indicates the presence of health data or disable transaction authentication if the signal indicates the absence of health data. For example, a smart watch may send its unique device ID and an indication that heart rate and/or pulse data was detected in response to a request to authenticate a transaction made with a credit card. The indication that heart rate data was detected may be a flag or some kind of message containing the indication sent from the smart watch or mobile device 430.

In an example embodiment, server 426 may receive a transaction request 440 from point of sale terminal 442, identify user account 428 based on information received with transaction request 440, determine whether transaction authentication is enabled or disabled for the user account, and either transmit signal 444 approving transaction request 440 if transaction authentication is enabled or transmit a signal 444 denying transaction request 440 if transaction authentication is disabled. For example, a user may swipe a card on a card reader in a store and the card reader may send a transaction request to a banking backend system. The banking backend system may determine the user's account and check if the user had set up a preference to authenticate transactions with this card using a wearable device, and, if so, use information about whether the wearable device is enabled or disabled in some way to approve or deny the purchase at the store.

In an example embodiment, developer tools and/or platform-based services may be used for various types of user devices. For example, an Apple Watch® may use the Apple® developer HealthKit. HealthKit may be used for requesting user permission to read, write and/or share, for example, heart rate samples and taking steps to maintain the privacy of user health data. Heart rate sample data may represent data at a particular point in time. Data structures such as sample classes to hold the sample data may include device, type, start date, end date, quantity samples, and correlations. The device may be the hardware device that generated the data stored in this sample. The type may be the sample type, such as a sleep analysis sample, a height sample, or a step count sample. The start date may be the sample's start time. The end date may be the sample's end time. If the sample represents a single point in time, the end time should equal the start time. If the sample represents data collected over a time interval, the end time should occur after the start time. Quantity samples may be data that can be stored as numeric values. Quantity samples may include the user's height and weight, as well as other data such as the number of steps taken, the user's temperature, and their pulse rate. Correlations may be composite data containing one or more samples and may be used to represent food and blood pressure data. IPhone® and Apple Watch® may each have their own HealthKit store and data may be automatically synced between the phone and watch. To save space, old data may be periodically purged from Apple Watch®.

For example, when reading data from HealthKit, a long-running query may run on an anonymous background queue. Long-running queries may continue to run in the anonymous background queue and provide updates whenever changes are made to the HealthKit store. An observer query may be a long-running query that monitors the HealthKit store and provides alerts for any changes to matching samples.

In an example embodiment, developer tools or platform-based services may be used for a fitness tracker such as FitBit®. A heart-rate API, which has a class HeartRateSensor and a HeartRateSensor API may be used to request permission to use query a heart rate monitor that measures the rate of a person's heartbeat. The API may provide access to the heart rate data, including a Boolean flag that indicates if the heart rate monitor is activated or not, event handlers, an interface BatchedHeartRateSensorReading for reading heartrate and timestamp, and an interface HeartRateSensorReading for real-time measurement from the heart rate monitor for reading heartrate and timestamp.

In other example embodiments, other developer tools or platform-based services may be used with IoT devices, wearable devices, and various other user devices for generating health data that may be used by an application for a different purpose.

Figure 5:
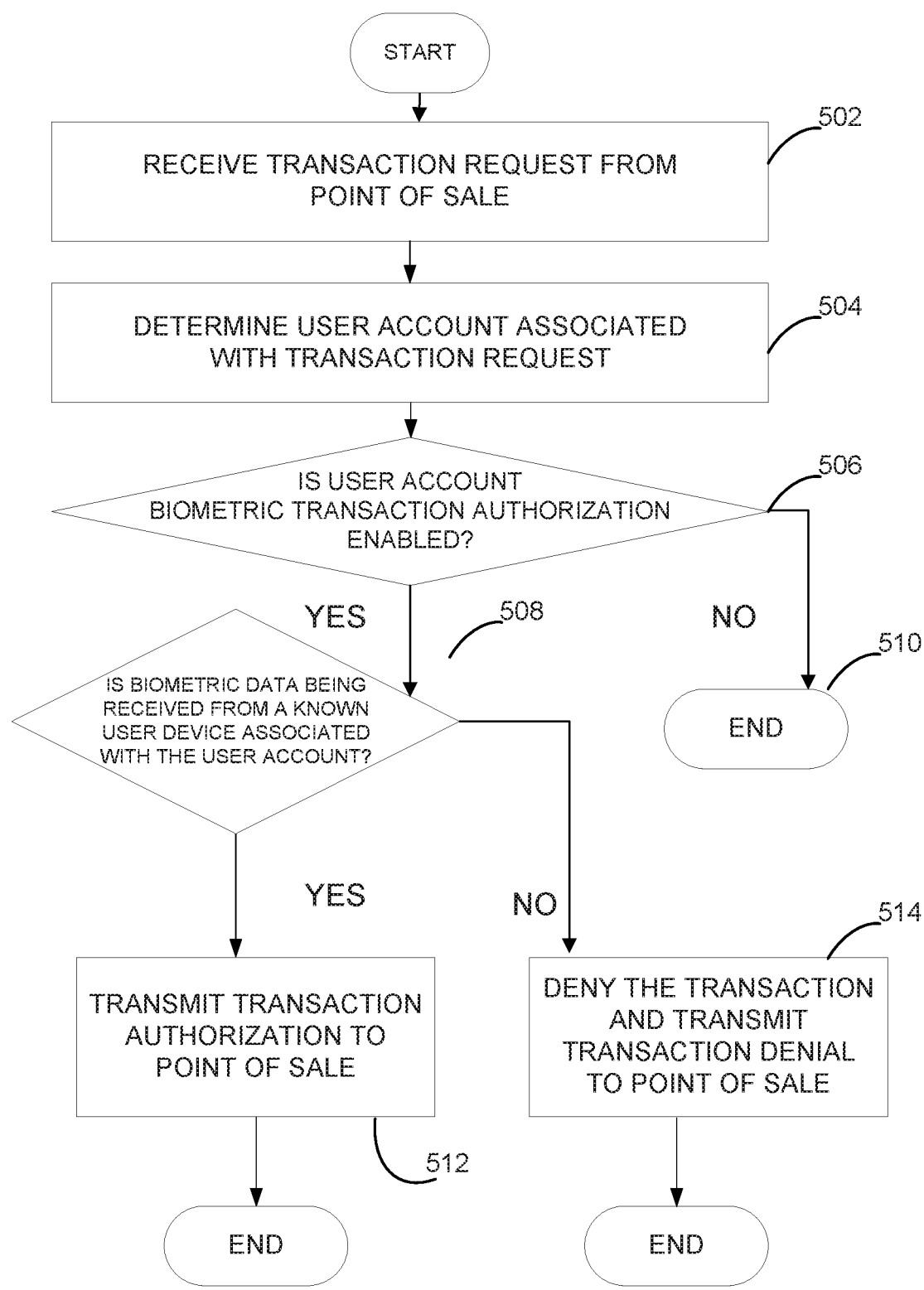
FIG. 5 is a flowchart illustrating a method for using a user device, according to an example embodiment.

FIG. 5 is a flowchart illustrating a method 500 for using a user device, according to an example embodiment. Method 500 begins at block 502. In block 502, a server may receive a transaction request from a point of sale terminal. For example, when a card holder pays a merchant for a purchase with a credit card, the point of sale terminal may process the transaction over a network including a bank backend server. As part of processing, the bank backend server may receive a message containing the transaction request. The transaction request may include the credit card details, merchant information and the payment amount. Credit card details may include the credit card number, card expiration date, billing address, card security code, etc. For example, when a user pays a merchant using a payment application on a smart watch, the point of sale terminal may processes the transaction so that a server may receive a message containing the transaction request and including similar information. For example, when a user pays a merchant using a payment application on a mobile phone, the point of sale terminal may processes the transaction so that a server may receive a message containing the transaction request and including similar information.

In block 504, the server may determine the user account associated with the transaction request. For example, a bank backend server may use credit card details in the transaction request to match to the card holder's account information stored in a database accessible by the bank backend server. For example, a bank backend server may use the credit card number from the transaction request as keys to index into or locate the card holder's account among the bank records. For example, a server in a credit card network may use credit card details in the transaction request to match to the card holder's account information stored in a database accessible by the credit card network.

In block 506, the server may determine whether the user account has biometric transaction authorization enabled. If the card holder does not have biometric transaction authorization enabled, then method 500 ends at 510. For example, the bank backend server may have previously stored information in the card holder's account information indicating that the card holder had enabled biometric transaction authorization. This information may include a unique identifier for a user device to provide biometric transaction authorization that was stored when the card holder registered the user device. For example, the user may register a fitness tracking device with a server and choose an option to use a biometric that is associated with the fitness tracking device to authenticate credit card purchases. For example, the fitness tracking device may provide heart rate, skin perspiration, skin temperature, and other biometrics that may be used for this and other purposes.

If in block 506 the user account has biometric transaction authentication enabled, then in block 508, the server may determine whether biometric data is being received from a known user device associated with the user account. For example, the bank backend server receives one or more messages from the user device including the unique identifier of the user device and biometric data from the user device. The bank backend server verifies the unique identifier of the user device by comparing the received unique identifier of the user device with the stored unique identifier of the user device in the cardholder's account. If they are the same, then biometric data is being received from the known user device. For example, a user had previously registered a smart watch with a server, including providing a unique smart watch identifier, which was stored by the server and associated with the user account. For example, a user had previously registered a medical device with a server, including providing a unique identifier associated with the medical device, which was stored by the server and associated with the user account.

In block 512, if biometric data is being received from the known user device, the server may authorize the transaction to the point of sale terminal. For example, a bank backend server may authorize the transaction by transmitting an authorization message to the point of sale terminal in response to the transaction request message from the point of sale terminal. For example, a bank backend server may receive biometric data from a medical device, such as a glucose monitor, which may provide some indication of glucose monitoring, and, in response, the server may authorize the transaction. For example, a bank backend system may authorize a transaction after receiving voice data from a headset device.

In block 514, if biometric data is not being received from the known user device, the server may deny the transaction to the point of sale. The bank backend server may check the last time a signal containing biometric data was received and use a measure of how stale the biometric data needs to be before transactions are declined. For example, if a signal is not received for x time period, then transactions will be denied until a new signal comes in. For example, the bank backend server may deny the transaction by transmitting a transaction denial message to the point of sale terminal in response to the transaction request message from the point of sale terminal. For example, a server may receive a message from a fitness tracker indicating the absence of biometric data and, in response, the server may deny the transaction. For example, a user might not be wearing a smart watch that was registered with the server and the server will receive an indication that the smart watch is not detecting a pulse so that the server may deny the transaction.

Figure 6:
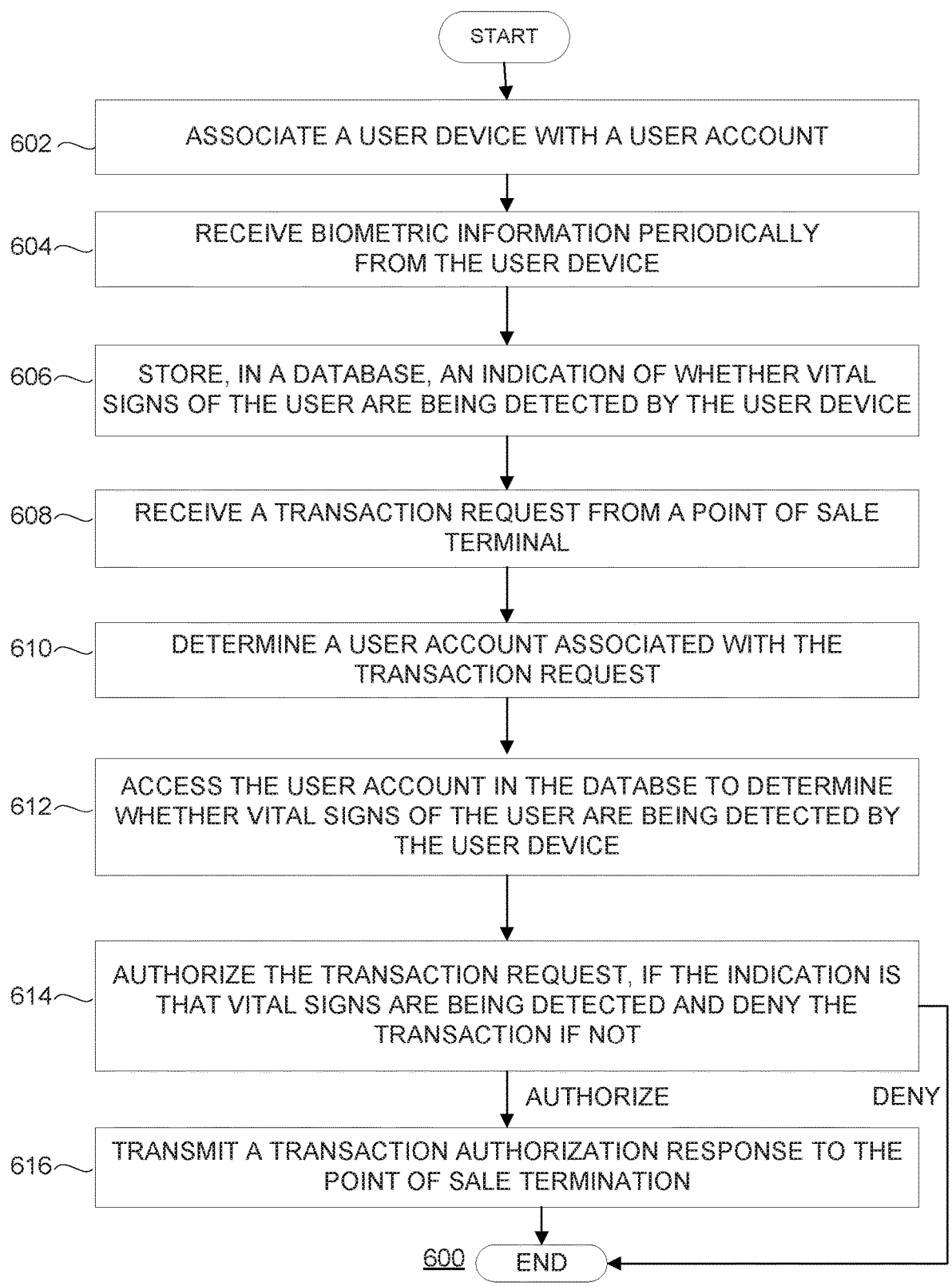
FIG. 6 is a flowchart illustrating a method for using a user device, according to an example embodiment.

FIG. 6 is a flowchart illustrating a method 600 for using a user device, according to an example embodiment. Method 600 begins at block 602. In block 602, the user device may be associated with a user account. For example, a smart watch may be capable of sensing health information of the user and transmitting that health information to a transaction authorization system. The transaction authorization system may include a server, a bank backend system and/or a point of sale terminal. The user may associate the smart watch with the user account by using a mobile phone to access an application that includes a way to register the smart watch with the bank backend system. The application may include providing a unique identifier associated with the smart watch to the bank backend system and providing credit card information to identify a user account to the bank backend system. The application may include selecting an option to use the smart watch to authenticate transaction made with that credit card. For example, a bank backend system may store information about the user account in a database, where the user account includes a record associating a fitness tracking device with the user account for the purpose of authenticating future transaction. For example, a smart watch may include an application for making payments that associates the smart watch with a payment account and may store this information in data storage on the smart watch or send the information for storage to a bank backend system or a mobile device. For example, a mobile device may include an application for making payments that associates a medical device with a payment account and may store this information on the mobile device or send the information for storage on a server.

In block 604, a user device may periodically provide biometric information that indicates whether vital signs of the user are being detected by the user device. Some of this biometric information may later be received by a server in a message sent by the user device. For example, a heart rate monitor may use a sensor to periodically read the heart rate of the user and store the readings in a data storage on the heart rate monitor. An application executing on the heart rate monitor may use an API to access the heart rate reading information. The application may later send a portion of the heart rate reading information to a server in a message. For example, a smart watch may be configured to monitor a pulse at the wrist of the wearer and store pulse reading data on the smart watch. An application executing on the smart watch may use an API to receive an alert when the pulse reading data changes on the smart watch. The application may later send an indication of a pulse reading change to a server in a message. For example, a medical device may be configured to periodically detect and store biometric information on the medical device. An application executing on the medical device may use an API to access the biometric information on the medical device. The application may later send a portion of the biometric information to a server in a message.

In block 606, an indication of whether vial signs of the user are being detected by a user device may be stored in a database or another type of data storage. For example, a smart watch may store an indication of whether a pulse is being detected at the wrist of the wearer in a memory on the smart watch. For example, a fitness tracker may store an indication of whether steps are being detected in a memory on the fitness tracker. For example, a medical device may store an indication of glucose monitoring in a memory on the medical device.

In block 608, a transaction request may be received from a point of sale terminal. For example, a card holder may swipe a card at a point of sale terminal to make a purchase at a restaurant. The point of sale terminal may process the purchase, resulting in a bank backend system receiving the transaction request, including credit card information, merchant information, and purchase amount, etc. For example, a user may use a payment application on a mobile device to request and pay for a service at a point of sale terminal. When the point of sale terminal processes the payment request, a server may receive a transaction request directly or indirectly from the point of sale terminal. For example, a credit card network may forward the transaction request to a server of an issuing bank.

In block 610, a server may determine a user account associated with a transaction request. For example, a banking back end server may receive a transaction request containing credit card information, payment amount, billing address, etc., and use this information to match to the appropriate user account in stored account records that are accessible by the server. For example, a server may query a database using a credit card number as an index. For example, a server may use a third party application to determine the user account associated with a transaction request. For example, a server may receive a transaction request contains information that uniquely identifies a user account, according to records at the server.

In block 612, a user account in a database is accessed to determine whether vital signs of a user are being detected by a user device. For example, an application executing on a smart watch may access a memory on the smart phone to determine whether a pulse was recently detected on the wrist of the user and then send a message to a server with the results. The server may receive the message and store a flag indicating whether vital signs of the user were being detected. The flag may be stored in a user account record in a database or in temporary storage for use in processing a current transaction. For example, a server processing a transaction authorization request may access a user account in a database to determine whether vital signs are being detected by a user device that was previously registered by the user. For example, a server may access a user account in a database to determine whether a user has selected an option of authenticating transactions using vital signs detected by a user device before processing a transaction authorization request.

In block 614, a transaction request is authorized if the indication is that vital signs are being detected and denied the transaction if not. If the transaction is denied, then the method 600 ends. For example, a bank backend server may send a message to a point of sale terminal that contains a transaction authorization after receiving a message from a smart watch indicating that a pulse was recently detected on the smart watch in response to an authentication request message sent by the bank backend server to the smart watch. For example, a server may authorize a transaction request by sending a message to a point of sale terminal upon receiving a message from a mobile phone indicating that vital signs are being detected on a user device. For example, a server may deny a transaction request upon receiving a message from a fitness tracker indicating that a heart rate is not being detected.

In block 616, a transaction authorization response may be transmitted to a point of sale terminal. For example, a bank backend server may send a transaction authorization response to a point of sale terminal. For example, a credit card network may send a transaction authorization response to a point of sale terminal, where the transaction authorization response was received and forwarded from another server.

Figure 7:
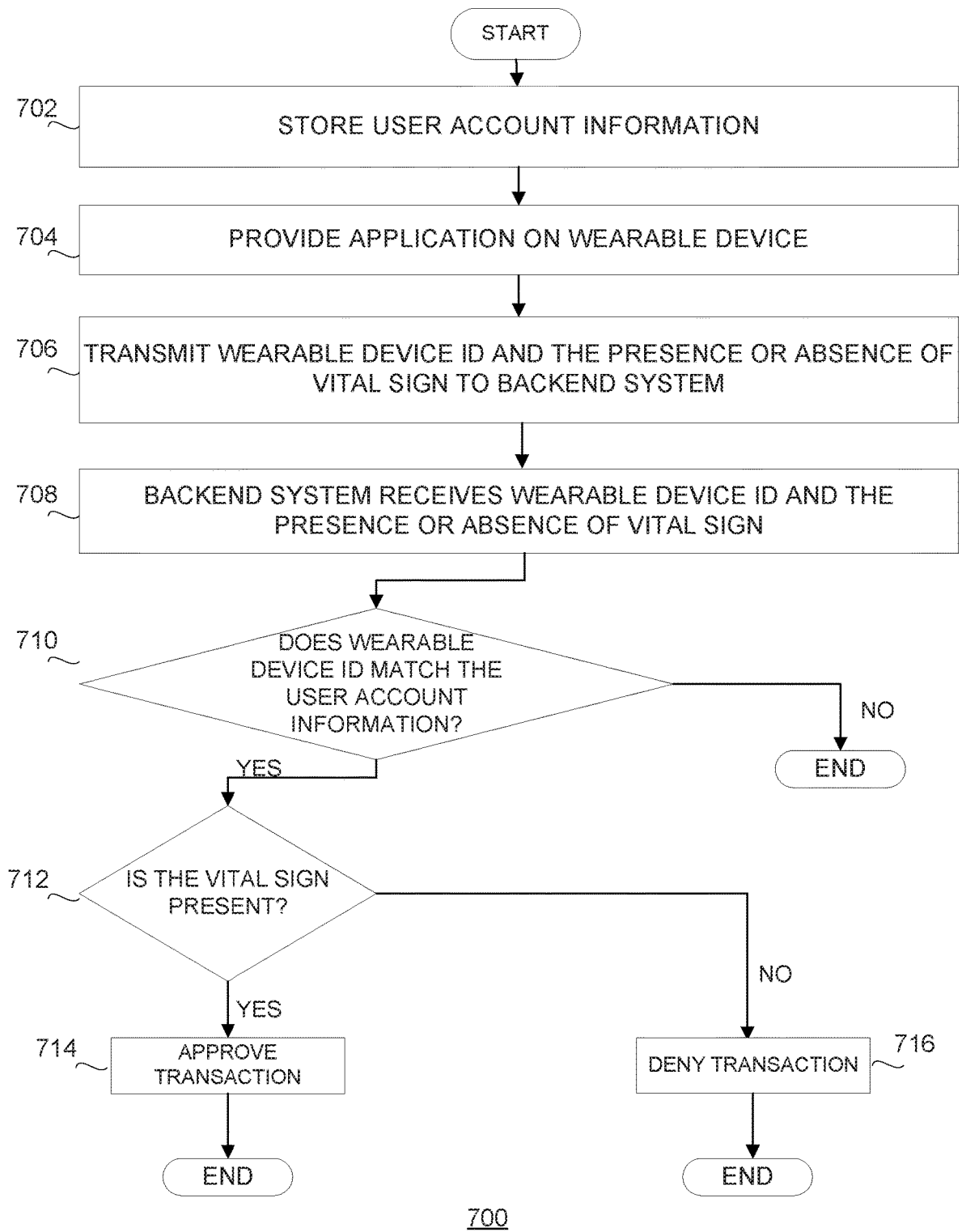
FIG. 7 is a flowchart illustrating a method for using a user device, according to an example embodiment.

FIG. 7 is a flowchart illustrating a method 700 for using a user device, according to an example embodiment. The method 700 begins at block 702. In block 702, user account information may be stored. For example, a bank backend system may store information about a user's credit card account in a record in a database. This information may include the credit card number, the user's name and billing address, etc. This information may also include information about whether the card holder elects to authenticate transactions using health information from a user device, such as a smart watch. For example, a user may register a smart watch with a bank backend system so that it may be used to authenticate future transactions. For example, each user account may have user account information that includes: information to identify the account holder, an account holder wearable device identifier, and a flag that indicates whether transactions are to be approved or denied based on the respective presence or absence of a vital sign of the account holder that is detected by a wearable device identified by the account holder wearable device identifier.

In block 704, an application may be provided on a wearable device. For example, an application may be provided for execution on a wearable device that includes a health monitor. The application may query, via an application programming interface to the health monitor, the wearable device to obtain a wearable device identifier and health data that indicates the presence or absence of a vital sign of the wearer of the wearable device. For example, a payment application may be installed on a smart watch that accesses health data monitored by smart watch through an application programming interface. For example, a fitness tracker may have an application provided that allows access to heart rate monitoring data. For example, a medical device may have an application provided that allows access to glucose monitoring data.

In block 706, the wearable device identifier and the presence or absence of vital signs may be transmitted wirelessly to a backend system. For example, a smart watch may wirelessly transmit the smart watch's unique identifier and health data that indicates the presence or absence of the wearer's pulse to a backend system in response to a request for authenticating a transaction. For example, a fitness tracker may send a message to a backend system that includes a unique identifier for the fitness tracker and an indication of the presence or absence of the wearer's heart rate during a recent period of time. For example, a medical device may send a message to a backend system that includes a unique identifier for the medical device and an indication of the presence or absence of recent glucose monitoring data.

In block 708, a backend system may receive a wearable device identifier and the presence of absence of a vital sign. For example, the backend system may receive a message from a smart phone including a unique identifier and an indication of the presence or absence of heart rate monitoring data. For example, the backend system may receive a message from a fitness tracker that includes a unique identifier and an indication of the presence or absence of motion detection data. For example, the backend system may receive a message from a mobile phone that includes a unique identifier or a medical device and an indication of the presence or absence of temperature data.

In block 710, a decision may be made about whether the wearable device identifier matches user account information. If it does not match, then the method 700 ends. For example, a processor at a backend system may match a smart watch identifier received in a message from the smart phone with the identifier of a previously registered smart watch that is stored at the backend system in a database record for an account holder associated with the registered smart watch. For example, a server may determine whether a fitness tracking device identifier sent in a message by the fitness tracking device matches the stored fitness tracking device identifier for a particular account holder identified in a transaction authorization request message received by the server. For example, a server may determine whether a medical device identifier sent in a message by the medical device matches a stored medical device identifier for an account holder identified in a transaction authorization request message received by the server from a point of sale terminal. The account holder may be determined by the server from credit card information and billing information in the transaction authorization request message and by matching that information to account records stored in a database accessible by the server. If the received medical device identifier and the stored medical device identifiers are different, then the method 700 ends.

In block 712, it is determined whether a vital sign is present. If the wearer's wearable device identifier matches the account holder wearable device identifier: access, using the processor at the backend system, the account holder user account, and set, using the processor at the backend system, the flag stored in the account holder user account that indicates whether transactions are to be approved or denied based on the received health data that indicates the presence or absence of the wearer's vital sign.

Figure 8:
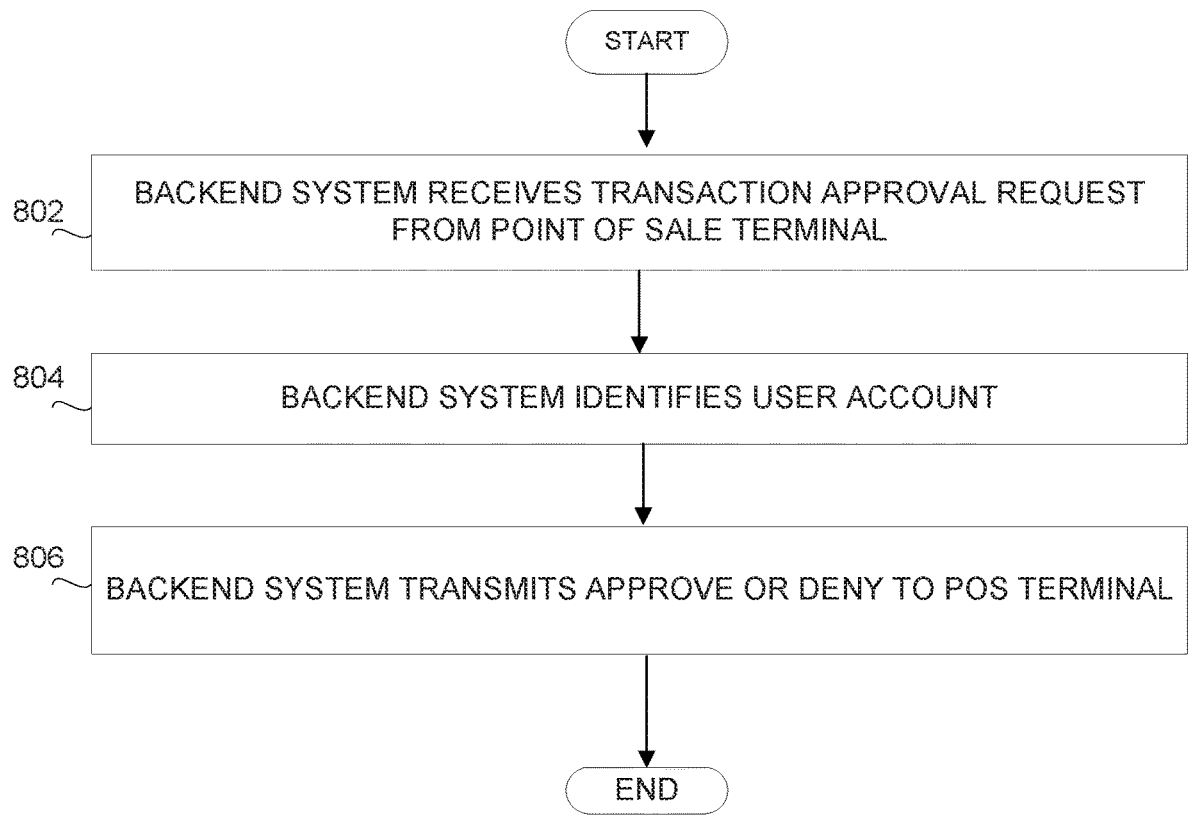
FIG. 8 is a flowchart illustrating a method for using a user device, according to an example embodiment.

FIG. 8 is a flowchart illustrating a method 800 for using a user device, according to an example embodiment. Method 800 begins at block 802. In block 802, a backend system receives a transaction approval request from a point of sale terminal. For example, the transaction approval request may include credit card information, transaction amount information, merchant information, the cardholder's billing address information, etc. In some embodiments, the backend system may receive the transaction approval request indirectly from the point of sale terminal and information may be forwarded from a credit card network. For example, the transaction approval request may be part of or in response to a payment authorization request.

In block 804 a backend system may identify a user account. A processor at the backend system may identify an account holder's account based on stored information already received about the user account while authenticating the transaction with health data from a user device.

In block 806, a backend system transmits a message to a point of sale terminal either approving or denying the transaction. A processor at the backend system may query the account holder user account to determine whether a flag stored in the account holder user account indicates whether to approve or deny the transaction. The processor at the backend system may transmit, based on the query result, a signal approving or denying the transaction to the point of sale terminal. The query may be an application executed by the processor to operate on a database holding user account records. The database may be accessible by the backend server or stored in memory on the backend server.

Figure 9:
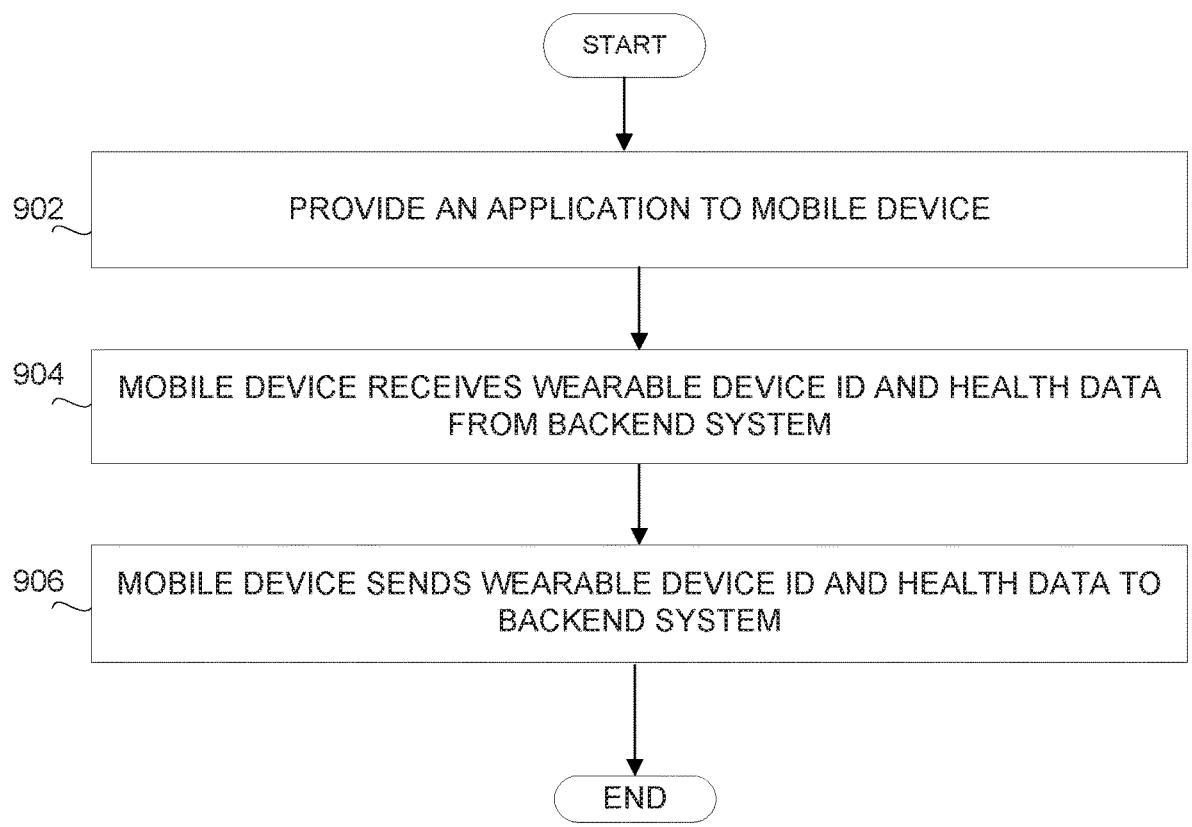
FIG. 9 is a flowchart illustrating a method for using a user device, according to an example embodiment.

FIG. 9 is a flowchart illustrating a method 900 for using a user device, according to an example embodiment. Method 900 begins at block 902. In block 902, an application is provided to a mobile device. The mobile device may be wirelessly connected to a wearable device. In block 904, the application on the mobile device may receive, via the wireless connection to the wearable device, the wearer's wearable device identifier and health data that indicates the presence or absence of the wearer's vital sign to the backend system. In block 906, the application may wirelessly transmit the received wearer's wearable device identifier and health data to the backend system. For example, a user may install a payment application on a mobile phone that is wirelessly connected to a smart watch. The application may provide a way for the user to register the smart watch, including sending a smart watch unique identifier to a backend system. The application may further provide a way for the smart watch to send health data to the backend system that indicates the presence of absence of a pulse on the wrist of the person wearing the smart watch to authenticate a future transaction made with the application.

Figure 10:
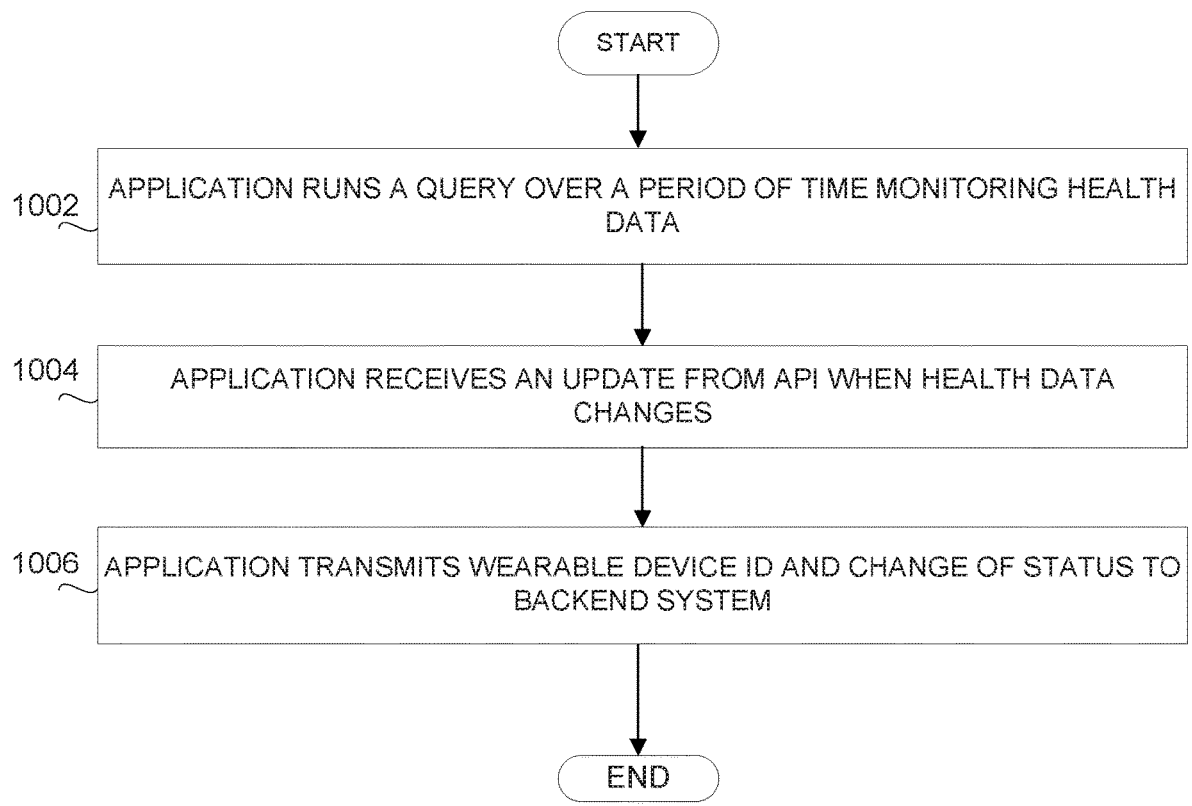
FIG. 10 is a flowchart illustrating a method for using a user device, according to an example embodiment.

FIG. 10 is a flowchart illustrating a method 1000 for using a user device, according to an example embodiment. Method 1000 begins at block 1002. In block 1002, an application may execute a query on a wearable device via an application programming interface. The query may be a long-running query that executes on an anonymous background queue on the wearable device. For example, a payment application on a smart watch may include a query from an API on the smart watch that monitors a heart rate periodically over a long period of time while other applications are running on the smart watch. The query may read and store heart rate data on the smart watch for future use for a payment-related purpose.

In block 1004, the application may receive an update from an application programming interface when the health data changes. For example, a smart watch application monitoring heart rate data, may be configured to receive alerts from another application when there is a change in status of the heart rate data, such as when the smart watch is put on or taken off the wrist of the user.

In block 1006, the application may transmit a wearable device identifier and a change of status signal to the backend system. For example, a smart watch application may send a smart watch unique identifier and a message including an indication that the heart rate data stopped being monitored when, for example, the user took off the smart watch or an indication that the heart rate data started being monitored when the user put on the smart watch.

Figure 11:
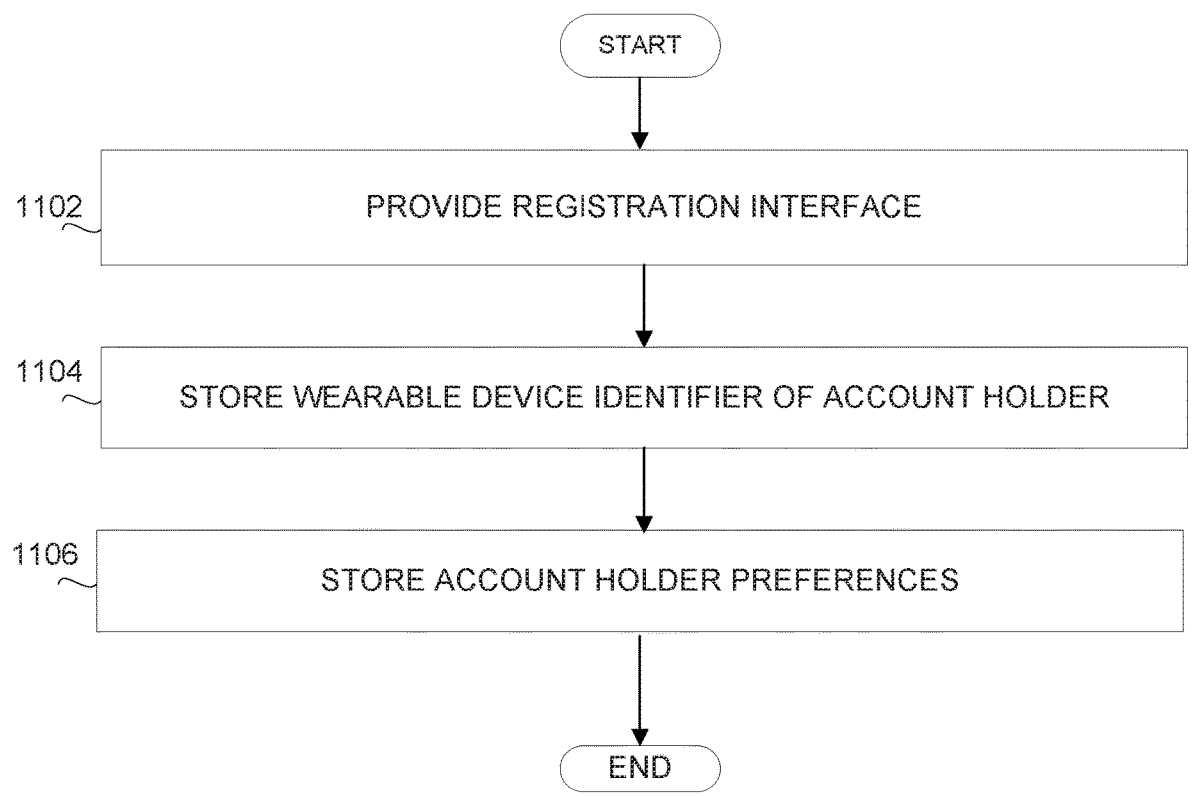
FIG. 11 is a flowchart illustrating a method for using a user device, according to an example embodiment.

FIG. 11 is a flowchart illustrating a method 1100 for using a user device, according to an example embodiment. Method 1100 begins at block 1102. In block 1102, a registration interface may be provided to an account holder. For example, a user may use a mobile phone to install a banking application that includes a way to register a wearable device to be used to authenticate payments from a particular credit card account. The banking application may include a registration interface for receiving and transmitting messages to a backend system via a wireless network. The messages may include a unique identifier for the wearable device that may be stored at the backend system to be used to authenticate future transactions. In block 1104, the backend server may store the account holder's wearable device identifier in the account holder's user account and/or in credit account records in a database accessible by the backend system. Other similar interfaces, e.g., web interfaces, associated with the backend system may be used to register a wearable device in a similar manner.

In block 1106, the backend server may store account holder preferences, such as a preference to use the wearable device to authenticate transactions made with a particular credit card account. For example, the banking application installed on a mobile phone may include a registration interface that includes a way to turn on an option to use a wearable device to authenticate transactions for a particular credit card so that the backend server will either approve or deny transactions based on the presence or absence of a vital sign from the wearable device around the time that a transaction is being processed for that credit card. The backend server may receive a message from the application on the mobile phone requesting to turn on the option to use the wearable device to authenticate transaction for that credit card. The backend server may then store information indicating that the account holder wants to use the wearable device to authenticate transaction in an account record associated with that credit card and stored in a database at the backend server.

Figure 12:
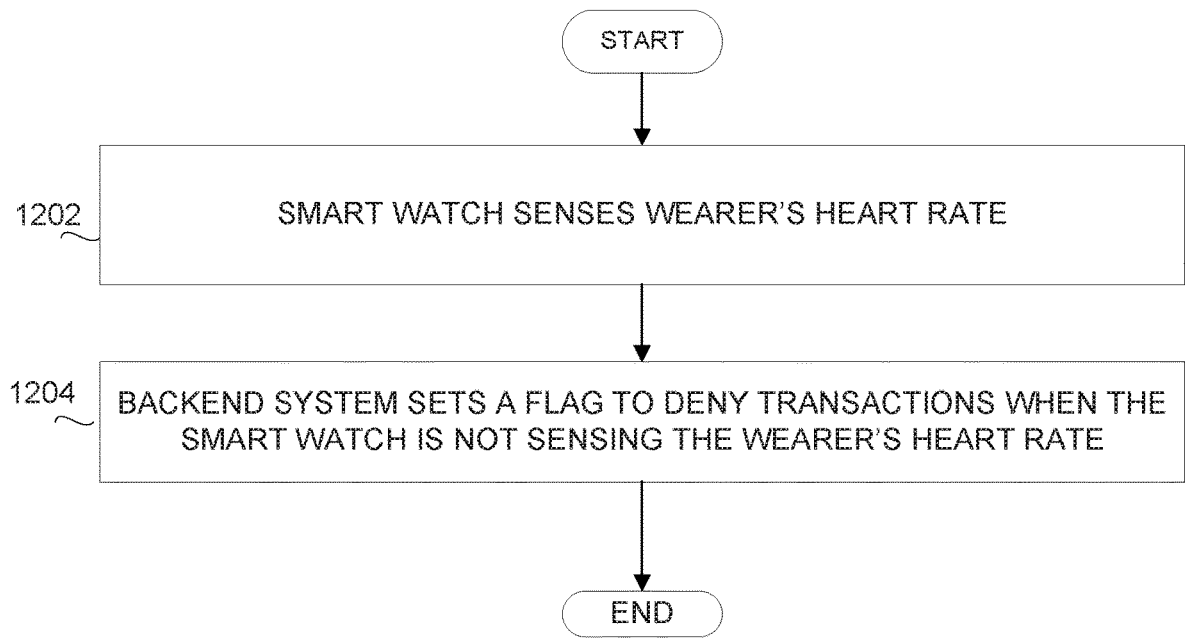
FIG. 12 is a flowchart illustrating a method for using a user device, according to an example embodiment.

FIG. 12 is a flowchart illustrating a method 1200 for using a user device, according to an example embodiment. Method 1200 begins at block 1202. In block 1202, a smart watch senses a wearer's heart rate. For example, a smart watch being worn by a wearer uses its optical heart rate sensors and associated software on the smart watch to detect and calculate the wearer's heart rate. For example, a smart watch may include an application that is capable of monitoring the wearer's heart rate and sending messages to a backend system that indicate the presence or absence of the wearer's heart rate. In block 1204, a backend system sets a flag to deny transactions when they smart watch is not sensing the wearer's heart rate. For example, the wearer may install an application on a smart watch that includes a registration interface. The registration interface may have a way for the smart watch to send messages to the backend system to register the smart watch. The registration interface may have a way for the smart watch to send message to the backend system to set a preference to approve or deny transactions based on the respective presence or absence of a vital sign, such as heart rate from the smart watch at the time of the transaction. Upon receiving the message setting this preference, the backend server may store a flag indicating this preference in an account associated with the wearer.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "some examples," "other examples," "one example," "an example," "various examples," "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrases "in one example," "in one embodiment," or "in one implementation" does not necessarily refer to the same example, embodiment, or implementation, although it may.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system, comprising:
   a server in data communication with a point of sale terminal;
   a user device of a user, wherein the user device is a wearable device, the user device comprising:
      a health monitor comprising sensors and associated software to obtain health information about a wearer of the user device, wherein the wearer is the user;
      a data storage storing user health data, wherein the user health data comprises the health information of the wearer of the user device;
      an application programming interface, wherein the application programming interface provides access to the health monitor and the user health data stored in the data storage; and
      an application, wherein the application comprises a payment application;
   wherein the user device is configured to:
      receive a request to authenticate a transaction;
      execute the application;
      obtain, via the executed application using a query, a user device identifier of the user device and the user health data stored in the data storage via the application programming interface;
      based on the obtained user health data, determine, via the executed application, the presence or absence of requisite health data; and
      in response to the request, transmit, via the executed application, the user device identifier and a signal, wherein the signal indicates the presence or absence of the requisite health data;
   wherein the server is configured to:
      store a user account of the user, wherein the user account comprises user account information, the user device identifier and a user preference, wherein the user preference is an indication to enable a biometric transaction authentication with the user device;
      receive the user device identifier and the signal indicating the presence or absence of the requisite health data;
      identify the user account based on the received user device identifier, wherein identifying the user account further comprises identifying the user preference comprised in the user account;
      determine whether the received signal indicates the presence or absence of the requisite health data, wherein the determining whether the received signal indicates the presence or absence of the requisite health data further comprises:
         enabling the biometric transaction authentication of the user account based on the user preference and the determining that the signal indicates the presence of the requisite health data and the user preference, or
         disabling the biometric transaction authentication of the user account based on the determining that the signal indicates the absence of the requisite health data;
   wherein the server is further configured to:
      receive a transaction request of the transaction from the point of sale terminal;
      identify the user account based on information received with the transaction request, wherein identifying the user account further comprises identifying the user preference of the user account;
      determine whether biometric transaction authentication is enabled or disabled for the user account, wherein determining that the biometric transaction authentication is enabled further comprises:
         sending the request to the user device to authenticate the transaction;
         receiving the signal indicating the presence of the requisite health data from the user device;
         approve the transaction request by transmitting an authorization message to the point of sale terminal based on determining that the biometric transaction authentication is enabled; or deny the transaction request by transmitting a transaction denial message to the point of sale terminal based on determining that the biometric transaction authentication is disabled.

2. The system of claim 1, further comprising:
a mobile device that is wirelessly connected to the user device;
wherein the user device is further configured to transmit the user device identifier and the signal indicating the presence or absence of the requisite health data to the mobile device;
wherein the mobile device is configured to:
receive the user device identifier and signal indicating the presence or absence of the requisite health data; and
transmit the user device identifier and signal indicating the presence or absence of the requisite health data to the server.

3. The system of claim 1, wherein the user device comprises an anonymous background queue, and the query is a long-running query that executes on the anonymous background queue on the user device,
wherein the user device is further configured to:
receive, via the executed application, an update associated with a change of the requisite health data; and
transmit the user device identifier and a change of status signal to the server, wherein the change of status signal comprises information of the update associated with the change of the requisite health data.

4. The system of claim 1, wherein the user device is a smart watch that detects and stores a vital sign of the wearer of the smart watch as the health information.

5. The system of claim 4, wherein, the health monitor includes a heart rate sensor, the user health data is sample heart rate data, and the server is associated with a bank backend system, wherein the server is further configured to approve a transaction based on the user device detects a heart rate at the time of the transaction.

6. The system of claim 1, wherein the signal indicating the presence or absence of the requisite health data is a Boolean flag.

7. The system of claim 1, wherein, via a user device registration process between the user device and the server, the server is configured to store the user device identifier and associate the user device with a user account of the wearer of the user device.

8. The system of claim 7, wherein, upon receipt of the user device identifier and signal indicating the presence or absence of the requisite health data, the server is further configured to:
compare the received user device identifier with the stored user device identifier;
determine whether the received and stored user identifiers are the same based on the comparison; and
enable the biometric transaction authentication based on determining that the signal indicates the presence of the requisite health data and the received and stored user identifiers are the same.

9. The system of claim 1, wherein receiving the user device identifier and the signal further comprises determining whether the signal is received within a predetermined time period, wherein approving the transaction request further comprises determining that the signal is received within the predetermined time period.

10. The system of claim 9, wherein the server is further configured to approve a second transaction request associated with the user account from the point of sale terminal based on determining that the biometric transaction authentication is enabled.

11. The system of claim 1, wherein:
the health monitor comprises a glucose monitor, and
the user health data comprises glucose monitoring.

12. A method using a system comprising a server in data communication with a point of sale terminal and a user device of a user, wherein the user device comprises a health monitor including sensors and associated software to obtain health information about a wearer of the user device, a data storage storing user health data of the wearer of the user device, an application programming interface providing access to the health monitor and the user health data in the data storage and an application, the method comprising:
storing, by the server, a user account of the user, wherein the user account comprises user account information, a user device identifier, and a user preference, wherein the user preference is an indication to enable a biometric transaction authentication with the user device;
receiving, by the server, a transaction request of a transaction from the point of sale terminal;
identifying, by the server, the user account based on information received with the transaction request, wherein identifying the user account further comprises identifying the user preference of the user account;
sending, by the server, a request to authenticate the transaction to the user device;
receiving, by the user device, the request to authenticate the transaction, wherein the user device is a wearable device of the user;
executing, by the user device, the application, wherein the application is a payment application;
obtaining, by the user device via the executed application using a query, the user device identifier of the user device and the user health data stored in the data storage via the application programming interface, wherein the user health data comprises the health information of the wearer of the user device;
based on the obtained user health data, determining, by the user device via the executed application, the presence or absence of requisite health data;
in response to the request, transmitting, by the user device via the executed application, the user device identifier and a signal to the server, wherein the signal indicates the presence or absence of the requisite health data;
receiving, by the server, the user device identifier and the signal indicating the presence or absence of the requisite health data from the user device;
identifying, by the server, the user account based on the user device identifier;
determining, by the server, whether the received signal indicates the present of the requisite health data;
enabling, by the server, the biometric transaction authentication of the user account based on the user preference and the determining that the signal indicates the presence of the requisite health data; and
approving, by the server, the transaction request by transmitting an authorization message to the point of sale terminal based on determining that the biometric transaction authentication is enabled for the user account.

13. The method of claim 12, wherein:
the health monitor comprises a heart rate monitor, and
the user health data comprises pulse monitoring.

14. The method of claim 12, wherein:
the user device is the wearable device, and the method further comprises:

upon removal by the user, transmitting, by the user device via the executed application, the user device identifier and a second signal to the server, wherein the second signal indicates the removal of the user device.

15. The method of claim 12, further comprising:
determining, by the server, a time of receipt of the signal; and
denying, by the server, the transaction until receipt of a new signal if the time exceeds a threshold.

16. A method using a system comprising a server in data communication with a point of sale terminal and a user device of a user, wherein the user device comprises a wearable device of the user comprising a health monitor including sensors and associated software to obtain health information about a wearer of the user device, a data storage storing user health data of the wearer of the user device, an application programming interface providing access to the health monitor and the user health data in the data storage and an application, the method comprising:
storing, by the server, a user account of the user, wherein the user account comprises user account information, a user device identifier, and a user preference, wherein the user preference is an indication to enable a biometric transaction authentication with the user device;
receiving, by the server, a transaction request of a transaction from the point of sale terminal;
identifying, by the server, the user account based on information received with the transaction request, wherein identifying the user account further comprises identifying the user preference of the user account;
sending, by the server, a request to authenticate the transaction to a mobile device;
receiving, by the mobile device, the request to authenticate the transaction;
transmitting, by the mobile device, the request to authenticate the transaction to the user device;
receiving, by the user device, the request to authenticate the transaction;
executing, by the user device, the application, wherein the application is a payment application;
obtaining, by the user device via the executed application using a query, the user device identifier of the user device and the user health data stored in the data storage via the application programming interface, wherein the user health data comprises the health information of the wearer of the user device;
based on the obtained user health data, determining, by the user device via the executed application, the presence or absence of requisite health data;
in response to the request, transmitting, by the user device via the executed application, the user device identifier and a signal to the mobile device, wherein the signal indicates the presence or absence of the requisite health data;
receiving, by the mobile device, the user device identifier and the signal;
transmitting, by the mobile device, the user device identifier and the signal to the server;
receiving, by the server, the user device identifier and the signal indicating the presence or absence of the requisite health data from the user device;
identifying, by the server, the user account based on the user device identifier;
determining, by the server, whether the received signal indicates the present of the requisite health data;
enabling, by the server, the biometric transaction authentication of the user account based on the user preference and the determining that the signal indicates the presence of the requisite health data; and
approving, by the server, the transaction request by transmitting an authorization message to the point of sale terminal based on determining that the biometric transaction authentication is enabled for the user account.

17. The method of claim 16, wherein via a user device registration process between the user device and the server, storing, by the server, the user device identifier and associating the user device with a user account of the wearer of the account.

18. The method of claim 16, wherein the query is executed on an anonymous background queue.

19. The method of claim 16, wherein the executed application periodically uses a query over a period of time.

20. The method of claim 17, further comprising:
prior to identifying the user account based on the user device identifier,
comparing, by the server, the user device identifier with the stored user device identifier; and
identifying, by the server, the user account based on the user device identifier if the user device identifier matches the stored user device identifier.

* * * * *